(12) United States Patent
Rothenberg

(10) Patent No.: US 11,780,871 B1
(45) Date of Patent: Oct. 10, 2023

(54) COVID-19 TREATMENT AND METHODS

(71) Applicant: Barry E. Rothenberg, Del Mar, CA (US)

(72) Inventor: Barry E. Rothenberg, Del Mar, CA (US)

(73) Assignee: BILLUPS-ROTHENBERG, INC., San Diego, CA (US)

( * ) Notice: Subject to any disclaimer, the term of this patent is extended or adjusted under 35 U.S.C. 154(b) by 105 days.

(21) Appl. No.: 17/215,839

(22) Filed: Mar. 29, 2021

Related U.S. Application Data

(60) Provisional application No. 63/005,136, filed on Apr. 3, 2020.

(51) Int. Cl.
*A61K 31/728* (2006.01)
*C07H 3/04* (2006.01)
*A61K 31/7084* (2006.01)
*A61K 45/06* (2006.01)

(52) U.S. Cl.
CPC ........... *C07H 3/04* (2013.01); *A61K 31/7084* (2013.01); *A61K 31/728* (2013.01); *A61K 45/06* (2013.01)

(58) Field of Classification Search
None
See application file for complete search history.

(56) References Cited

PUBLICATIONS

Hellman et al., Journal of Biological Chemistry, 2020, 295(45), pp. 15418-15422. (Year: 2020).*

* cited by examiner

*Primary Examiner* — Traviss C McIntosh, III
(74) *Attorney, Agent, or Firm* — Umberg Zipser LLP

(57) ABSTRACT

Compositions and methods are presented that reduce the risk for ARDS and/or need for ventilation in a patient diagnosed with a coronavirus, and particularly SARS-CoV-2 virus, a SARS virus, or a MERS virus. In preferred aspects, HMW-HA is administered to the lung before onset of ARDS and/or cytokine storm. Additionally, NAD+ may be co-administered or prophylactically administered where NAD$^+$levels are low.

14 Claims, No Drawings

COVID-19 TREATMENT AND METHODS

This application claims priority to our co-pending U.S. Provisional Patent Application with the Ser. No. 63/005,136, which was filed Apr. 3, 2021, and which is incorporated by reference herein.

FIELD OF THE INVENTION

The present disclosure relates to composition and methods of treating an individual that is diagnosed with a coronavirus infection, and particularly as it relates to reducing the severity or escalation of symptoms associated with the coronavirus (e.g., SARS-CoV-2) infection.

BACKGROUND OF THE INVENTION

The background description includes information that may be useful in understanding the present disclosure. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

After several noteworthy coronavirus outbreaks in the recent years, including SARS and MERS, SARS-CoV-2 is yet another example of a serious infectious disease precipitated by a member of the coronavirus family. While diagnostic tests have become available in relatively short time, numerous attempts to treat or mitigate the disease have so far not had significant success. Most typically, patients with severe symptoms are treated to maintain respiration/blood oxygenation, and supportive treatment is provided to reduce or prevent multi-organ damage or failure. Despite such interventions, the mortality rate is significant, particularly in elderly, immune compromised individuals, and individuals with other underlying conditions, including heart disease, lung disease, or diabetes.

Indeed, a clear understanding of causative factors contributing to the increased severity of COVID-19 in patients with underlying medical conditions seems to be largely absent. This lack of understanding is likely contributing to the inability to identify therapeutic compounds that are effective and safe in reducing damaging pathologies observed in this disease. There is an immediate need to identify therapeutic compounds and develop delivery protocols that will reduce severity of the pathology without appreciably altering the protective acquired immune response.

Thus, even though various methods of addressing symptoms in patients with COVID-19 are known in the art, all or almost all of them suffer from various disadvantages. Consequently, there is a need to provide improved compositions and methods that provide therapeutic effect, that reduce or prevent an exacerbated immune response and/or cytokine storm. Viewed from a different perspective, there is a need to reduce the severity of an escalating immune response that would otherwise lead to significant tissue and organ damage, particularly in individuals that have underlying health conditions that render such individuals susceptible to such damage. Indeed, dampening an escalating immune response would reduce, or even avoid the need for ventilators in COVID-19 patients.

Thus, even though various methods are known in the art to support physiological functions in a patient infected with SARS-CoV-2, all or almost all of them suffer from various disadvantages. Consequently, there is still a need to provide improved compositions and methods that reduce or prevent an exacerbated immune response and to so avoid or reduce organ damage and the need for ventilators in COVID-19 patients.

SUMMARY OF THE INVENTION

The inventor has now discovered that an exacerbated immune response against SARS-CoV-2 can be reduced or even entirely avoided by providing one or more therapeutic agents to a patent diagnosed as being infected by SARS-CoV-2 but prior to escalation of the patient's immune response.

In one aspect of the inventive subject matter, the inventor contemplates a method of treating an individual infected with a respiratory virus that includes a step of administering, upon or after confirmation of the infection, to the lung of the individual a composition that comprises a high-molecular weight hyaluronic acid (HMW-HA), wherein administration is performed prior to onset of acute respiratory distress syndrome or cytokine storm.

Likewise, the inventors contemplate a method of reducing the likelihood for the need for ventilation of an individual infected with a respiratory virus that includes a step of administering, upon or after confirmation of the infection, to the lung of the individual a composition that comprises a high-molecular weight hyaluronic acid (HMW-HA), wherein administration is performed prior to onset of acute respiratory distress syndrome or cytokine storm.

In some embodiments, the respiratory virus is a coronavirus (e.g., SARS-CoV-2 virus, SARS virus, MERS virus). In further embodiments, the HMW-HA has a molecular weight of between 1,000 and 3,000 kDa, and is preferably administered as an inhaled composition or in a lavage fluid.

It is also contemplated that the HMW-HA is administered between 0 and 7 days of confirmation of the infection, preferably in an amount effective to dampen an immune response in the lung of the individual. Where desired, $NAD^+$ or a $NAD^+$ precursor (e.g., nicotinamide riboside) may be administered. Additionally, or alternatively, pterostilbene or other SIRT-pathway stimulants (e.g., quercetin, etc.) may be administered to increase NAD in the human.

Therefore, and viewed from a different perspective, the inventor also contemplates an HMW-HA composition for use in reducing severity of acute respiratory distress syndrome in a patient diagnosed with a coronavirus infection, and/or an HMW-HA composition for use in reducing a likelihood for a need for ventilation of an individual infected with a respiratory virus.

Various objects, features, aspects, and advantages will become more apparent from the following detailed description of preferred embodiments.

DETAILED DESCRIPTION

The inventor has now discovered certain mechanisms that cause severe pathology prior to and during the SARS-CoV-2 infection and aligns the observed molecular and cellular events with the disease timeline. More particularly, the inventor postulates that the 'ground glass' X-ray that is seen in as few as 3-4 days after onset of COVID-19 patients symptoms, is caused by prior long-term chronic stimulation of pro-inflammatory M1 macrophages and the resulting new recruitment of innate immune cells (e.g., neutrophils). Between days 10 and 12 of the infection, viral antigen specific IgG appears and attaches to the surface Fc receptor of the macrophages, thus arming the cytokine rich innate immune cells that are already present in an excessive quantity (e.g., due to smoking, aerosol-induced lung damage, etc.) relative to a healthy patient without chronic stimulation of pro-inflammatory M1 macrophages. Once these cells contact the viral antigens, they immediately release cytokines, resulting in a destructive cytokine storm. Consequently, one significant aspect of contemplated COVID-19 treatments is to dampen this initial inflammatory response without interfering with the protective T and B cell acquired immune response phase.

In this context it is important to recognize that the damage to other organs in late stages of COVID-19 appears to be the result of a breakdown of the hyaluronic acid (HA) physical barrier protecting alveoli cell wall fibrous structural components, including elastin fibers. When this structure is damaged, the alveoli cell walls become leaky allowing for the rapid release of armed neutrophils, which will then precipitate further damage outside the lung. It should also be appreciated that most of the cellular and metabolic factors associated with increased risk for prolonged and severe complications from COVID-19 have common metabolic and immunologic characteristics. Specifically, the similarities are: (1) polarization of M1 and M2 macrophages of the innate immune system; and (2) decreased intracellular NAD$^+$ levels. Notably, both of these characteristics accompany inflammation.

Based on the above considerations and further observations below, the inventor discovered that there are various readily available compounds/compositions to address these characteristics: (1) commercially available nutritional supplements that have been shown to increase cellular NAD$^+$ levels; and (2) an inhalable aerosol form of hyaluronic acid (HA) (an FDA approved drug) that has successfully been used to treat cystic fibrosis. Moreover, an aerosol form of high-molecular weight (HMW)-HA inhaled twice a day has been shown by others to play a protective role in reducing elastin degradation. Advantageously, such agents are inexpensive, safe, readily available, and are simple to administer. In particular, one or more agents may be given to an individual to increase levels of nicotinamide adenine dinucleotide (NAD$^+$) in a subject, which may be done prophylactically or upon diagnosis of SARS-CoV-2 infection; and high molecular weight-hyaluronic acid (HMW-HA) may be administered upon a positive test for the SARS-CoV-2 but prior to an escalating immune response (e.g., immediately after diagnosis). The following provides further details and aspects of contemplated methods. However, while the present disclosure generally refers to SARS-CoV-2, infections with respiratory viruses other than coronaviruses (e.g., rhinoviruses, adenoviruses, respiratory syncytial viruses, influenza viruses, parainfluenza viruses, parvoviruses, etc.) are expressly contemplated in conjunction with the teachings presented herein, particularly where such viral infections lead to acute respiratory distress syndrome (ARDS).

Prophylactic Increase in NAD$^+$ Levels

NAD$^+$ is a naturally occurring coenzyme synthesized in all cells. It is found in two forms: either oxidized (NAD$^+$) or reduced (NADH). The NAD$^+$/NADH ratio is tightly controlled in the body, and its imbalance can lead to clinical pathologies. Notably, all of the underlying risk factors for COVID-19 as noted below are associated with lowered levels of intracellular NAD$^+$. For example, the age-associated decline of NAD$^+$ levels in many tissues is the result of cellular senescence and increased inflammation. In addition, others have shown that reduced levels of NAD$^+$ typically accompanies increased polarization of inflammatory CD38$^+$ M1 macrophages. Thus, it should be recognized that NAD$^+$ supplements (and other forms of NAD$^+$ delivery to an individual) are recommended to be taken prophylactically by all individuals with underlying inflammatory conditions. This could reduce the risk of experiencing excessive inflammation of the lungs and other organs if they contract COVID-19.

Some of the underlying conditions that put COVID-19 patients at a higher risk for severe pathology include advanced age (e.g., >60 yr) and patients diagnosed or suspected to have diabetes, asthma, hypertension (patients on high blood pressure medications, e.g. ACE2 inhibitors and Ca+channel blockers), atherosclerosis, rheumatoid arthritis, pulmonary disease (e.g., COPD and idiopathic pulmonary fibrosis (IPF), particle sizes equal to or less than 2.5 µm). This group includes smokers (including smokers of marijuana and inhaled recreational drugs, and possibly vapers), and individuals exposed to diesel exhaust and air pollution (e.g., industries which produce an abundance of air borne 2.5 µm particles as with coal fired power plants).

There are several distinct populations of cells residing in the lungs that belong to the innate arm of the immune system. For brevity, this discussion will focus on the coordinated inflammatory effects of M1 and M2 macrophages. Pro-inflammatory M1 macrophages are derived from M2 macrophages and are responsible for killing pathogens. While the anti-inflammatory M2 macrophages heal or repair tissues, the M2 cells also play an anti-tumor phagocytic role. M1/M2 macrophages are part of the innate immune system and have a central role in activating T and B cell adaptive immune responses. Polarization of M1 and M2 macrophages is a key component in the progression of serious pulmonary pathology. Besides virus-induced lytic damage, rapid viral replication induces M1 polarization and inflammation, which are the two main causes of lung damage. Healing M2 macrophages produce the immunosuppressive cytokine IL-10, which down-regulates the production of various M1 pro-inflammatory cytokines such as IFNγ, TNFα, IL-1β and IL-12.

Administration of HMW-HA Upon COVID-19 Diagnosis

Hyaluronic acid (HA) is a disaccharide polymer made up of the repeating D-glucuronic acid and N-acetylglucosamine units. HA and elastin fibers play a critical role in maintaining the lung matrix structure. This is especially true in the alveolar cells, where HA surrounds and protects elastin fibers. In this context, it should be especially appreciated that HA polymers have multiple effects depending on size. More particularly, HA polymers with a molecular weight of between 1000 kDa and 3000 kDa are effective in polarizing M2 macrophages, increasing the M2 macrophage production of IL-10 and suppressing the output of damaging cytokines produced by M1 cells. High molecular weight HA (HMW-HA greater >1000 kDa) has been used to reverse pulmonary inflammation and damage in particle induced (size 2.5 µm) lung inflammation in a mouse model. Furthermore, an inhalable aerosol form of high molecular weight hyaluronic acid (HMW-HA) has been demonstrated to be safe and effective in slowing the progression of Chronic Obstructive Pulmonary Disease (COPD) in humans. COPD includes bronchitis and emphysema. There are multiple contributing factors to COPD such as farmer's lung resulting from inhalation of plant derived mold. Other reports show a clear association with small sized particles <2.5 µm produced by smoking, flour dust, and coal powered energy plants.

When acute viral-induced inflammatory activation continues, it will lead to excess lymphocyte pulmonary recruitment, including polarization of M1 cells and neutrophils, another distinct cell type of the innate immune system. Recruitment of these cell types leads to increased inflammatory cytokine production and release. Unfortunately, this process initiates large-scale enzymatic fragmentation of HMW-HA, resulting in accumulation of low molecular weight inflammatory HA, which in turn further stimulates activity of M2 macrophages and neutrophils. The outcome of this cellular and molecular process is severe pulmonary damage and ultimately death. Furthermore, ventilator-induced lung injury may be an added physical concern in HMW-HA degradation and subsequent inflammatory response.

It should be particularly appreciated that the biochemical activity of HA is dependent on polymer length. Length influences cell receptor binding and altered gene expression: HMW-HA is known to be the ligand for the M2 cell surface receptor CD44. Binding of HMW-HA to CD44 stimulates the production of an anti-inflammatory cytokine, IL-10. Shorter length HA polymers have the opposite effect, by suppressing IL-10 production. HMW-HA has been previously demonstrated to be effective when administered to cystic fibrosis patients twice a day for 28 days and did not have reported adverse effects.

In addition, it should be noted that the timing of HMW-HA intervention is of significance as earlier administration of HMW-HA improves the odds of reducing buildup of large numbers of inflammatory cells, resulting in reduced pulmonary damage and limiting the need for ventilation. As will be readily appreciated, HMW-HA is therefore not an antiviral drug for treatment of COVID-19, but rather a stop-gap measure intended to reduce the projected pressures on healthcare systems (e.g., supportive treatments, ventilation, etc.).

Viewed from a different perspective, the rapid pulmonary injury seen between days 10-14 in COVID-19 patients may be the result of earlier M1 recruitment of various cell types of the innate immune system. These include natural killer cells, neutrophils, and increased polarization of M1 macrophages. The switch from IgM to IgG antibody production around day 10 of the infection would allow for the anti-viral antigen specific IgG arming of the rapidly accumulating innate effector cells. This simple explanation accounts for the enhanced release of destructive cytokines, which explains the rapid destruction (sometimes in as little as 4 hours) of pulmonary tissue as seen in CAT-scans of COVID-19 patients. The model is testable by collecting lavage samples prior to and during HMW-HA administration and identifying accumulating numbers of each innate cell type through the entire course of treatment and recovery.

Predisposing Genetic Factors

The inventor also observed that there may be genetic factors that predispose COVID-19 patients for severe pulmonary pathology. In the 2003 SARS-CoV epidemic, Taiwanese researchers noticed a significant number of SARS-CoV patients with severe pulmonary disease that did not seem to have any underlying condition, such as age or smoking, which would have put them at higher risk for disease pathology. They therefore screened this population for HLA class 1 association. Their data identified two HLA alleles that were significantly elevated in this patient group. They were HLA-B*46:01 and HLA-C*15:01. HLA-B*46:01 was formed by a gene conversion event between HLA-B*15:01 and HLA-C*01:0. With this knowledge they immediately tested front line healthcare workers and identified individuals expressing these alleles. Once identified, they were removed from direct contact with COVID-19 patients and exposure to SARS-CoV.

Exemplary Compositions And Methods

In view of the above, the inventor contemplates that all compositions that increase $NAD^+$ levels are deemed suitable for use herein. Such $NAD^+$ increase will typically be achieved by administering a prodrug form or precursor that can be metabolized to $NAD^+$. Most preferably, such compositions include nutraceutical and pharmaceutical compositions, which may be administered in any suitable routs, and most preferably via oral or parenteral route. For example, suitable supplements include niacin, nicotinamide riboside, NAD per se, and further compounds and precursors as described, for example, in WO2018030389, WO201924298, US20190382436, WO2005115428, US20170266218, WO2019053518, and U.S. Pat. No. 10,392,414, all incorporated by reference herein.

Most typically, the compositions that increase $NAD^+$ levels will be administered in known and generally acceptable dosage level known for the composition. Therefore, suitable dosage levels will typically be between 10-100 mg/day, or between 100-200 mg/day, or between 200-600 mg/day, or between 600-1,000 mg/day, and even higher. Administration is preferably performed daily, or at least twice a week, or at least weekly, etc., preferably for a period of at least one week, or at least two weeks, or at least one month, or at least 1 year where administration is prophylactically. On the other hand, where the administration commences at the time of COVID-19 diagnosis or determination of infection with SARS-CoV-2, administration is at least every other day, or daily, or at least twice daily, or even continuously over at least several hours in case of infusion. In such cases, the daily dosage may be higher, such as between 200-400 mg/day, or between 400-800 mg/day, or between 800-1,500 mg/day, and even higher.

With respect to suitable HA formulations it is generally preferred that the HA is a HMW-HA, typically with a molecular weight of between 1,000 kDa and 3,000 kDa. Moreover, the HMW-HA may be crosslinked (e.g., via urea), branched, or linear. While not limiting to the inventive subject matter, the HMW-HA is administered directly into the lung, preferably in an aerosolized form and optionally on a carrier. On the other hand, the HMW-HA may also be administered to the lung via injection or lavage as best suitable or tolerated by the patient. With respect to suitable dosages, it is generally preferred that the HMW-HA administration 100 mg to 300 mg per dose, or between 300 mg to 600 mg per dose, or between 600 mg to 1,000 mg per dose, or between 1,000 mg to 3,000 mg per dose, or between 3,000 mg to 5,000 mg per dose, or even higher. The PHOSITA will be readily able to determine the proper dosage based on known uses of inhalable HMW-HA and severity of the condition of the patient. In addition, it is also contemplated that inhibitors of hyaluronidase may be administered to the patient to reduce the degradation of HMW-HA. For example, contemplated inhibitors include L-Ascorbic Acid 6-Hexadecanoate, high molecular mass poly (styrene-4-sulfonate), fenoprofen, gossypol, sodium aurothiomalate, glycerrhizic acid, fatty acids, plant-derived compounds, heparin, and O-sulfated HA (sHA).

It is further contemplated that the HMW-HA and $NAD^+$ may be co-administered or administered separately (e.g., sequentially), and the mode of co-administration is not deemed critical at this juncture. Indeed, sole administration of HMW-HA may be performed, particularly where levels of $NAD^+$ are deemed within physiological concentrations. However, it is generally preferred that the administration of HMW-HA is performed upon confirmation of SARS-CoV-2 infection, and most typically before onset of symptoms or before escalation of the immune response. Therefore, in most cases, administration will commence within one day, or within two days, or within three-five days, or within five to nine days, or within six to twelve days from the date of confirmation of SARS-CoV-2 infection. Viewed from a different perspective, HMW-HA (and $NAD^+$) administration will be prior to development of ARDS or cytokine storm.

In still further contemplated aspects, it should also be noted that the compositions presented herein can be employed to treat long-haul individuals that exhibit ongoing symptoms or that exhibit post initial recovery (and possibly viral clearance) one or more long-haul symptoms, including fatigue, shortness of breath, difficulty breathing, blood clots, muscle or body aches, and/or difficulty concentrating. Most typically treatment may commence (or continue beyond) at least 14 days after confirmation of the infection to thereby treat long-haul symptoms, and may be continued for at least 7 days, or at least 14 days, or at least one month, or even longer. Still further, it is contemplated that HMW-HA can be administered by injection (e.g., into a joint such as knee or shoulder) to so reduce inflammation via modulation of the macrophage population.

As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.). It should further be noted that the terms "prognosing" or "predicting" a condition, a susceptibility for development of a disease, or a response to an intended treatment is meant to cover the act of predicting or the prediction (but not treatment or diagnosis of) the condition, susceptibility and/or response, including the rate of progression, improvement, and/or duration of the condition in a subject.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the full scope of the present disclosure, and does not pose a limitation on the scope of the invention otherwise claimed. No language in the specification should be construed as indicating any non-claimed element essential to the practice of the claimed invention.

It should be apparent to those skilled in the art that many more modifications besides those already described are possible without departing from the full scope of the concepts disclosed herein. The disclosed subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of treating an individual infected with a respiratory virus, comprising:
   upon or after confirmation of the infection, administering to a lung of the individual a composition comprising a high-molecular weight hyaluronic acid (HMW-HA) having a molecular weight of at least 1,000 kDa; and
   wherein administering is performed prior to onset of acute respiratory distress syndrome or cytokine storm.

2. The method of claim 1 wherein administration of the composition reduces a likelihood for a need for ventilation of the individual.

3. The method of claim 1 wherein the respiratory virus is a coronavirus.

4. The method of claim 1 wherein the respiratory virus is a SARS-CoV-2 virus, a SARS virus, or a MERS virus.

5. The method of claim 1 wherein the HMW-HA has a molecular weight of between 1,000 and 3,000 kDa.

6. The method of claim 1 wherein the composition is administered by inhalation.

7. The method of claim 1 wherein the composition is administered by pulmonary lavage.

8. The method of claim 1 wherein administering the composition is performed between 0 and 7 days of confirmation of the infection.

9. The method of claim 1 wherein the composition is administered in an amount effective to dampen an immune response in the lung of the individual.

10. The method of claim 1 wherein the composition is administered in an amount effective to prevent a cytokine storm.

11. The method of claim 1 further comprising administering $NAD^+$ or a $NAD^+$ precursor.

12. The method of claim 11 wherein the $NAD^+$ precursor is nicotinamide riboside or a sirtuin pathway simulant.

13. A method of treating an individual infected with a respiratory virus, comprising:
   upon or after confirmation of the infection, administering to a lung of the individual a composition comprising a high-molecular weight hyaluronic acid (HMW-HA) having a molecular weight of at least 1,000 kDa; and
   wherein administering is performed at least 14 days after confirmation of the infection to thereby treat long-haul symptoms.

14. The method of claim 13 wherein the long-haul symptoms are fatigue, shortness of breath, difficulty breathing, blood clots, muscle or body aches, and/or difficulty concentrating.

\* \* \* \* \*